United States Patent
Mathai et al.

(10) Patent No.: US 12,125,213 B2
(45) Date of Patent: Oct. 22, 2024

(54) SYSTEM AND METHOD FOR VESSEL SEGMENTATION

(71) Applicants: Carnegie Mellon University, Pittsburgh, PA (US); University of Pittsburgh—Of the Commonwealth System of Higher Education, Pittsburgh, PA (US)

(72) Inventors: Tejas Sudharshan Mathai, Seattle, WA (US); John Galeotti, Pittsburgh, PA (US); Vijay Saradhi Gorantla, Winston Salem, NC (US)

(73) Assignees: Carnegie Mellon University, Pittsburgh, PA (US); University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 403 days.

(21) Appl. No.: 17/618,151

(22) PCT Filed: Jun. 12, 2020

(86) PCT No.: PCT/US2020/037495
§ 371 (c)(1),
(2) Date: Dec. 10, 2021

(87) PCT Pub. No.: WO2021/006991
PCT Pub. Date: Jan. 14, 2021

(65) Prior Publication Data
US 2022/0284589 A1      Sep. 8, 2022

Related U.S. Application Data

(60) Provisional application No. 62/860,381, filed on Jun. 12, 2019.

(51) Int. Cl.
| | | |
|---|---|---|
| G06T 7/149 | (2017.01) | |
| A61B 6/50 | (2024.01) | |
| G06T 7/00 | (2017.01) | |
| G06T 7/12 | (2017.01) | |
| G16H 30/40 | (2018.01) | |

(52) U.S. Cl.
CPC ............ G06T 7/149 (2017.01); A61B 6/504 (2013.01); G06T 7/0012 (2013.01); G06T 7/12 (2017.01);
(Continued)

(58) Field of Classification Search
CPC .......... G06T 7/0012; G06T 7/10; G06T 7/12; G06T 7/13; G06T 7/149; G06T 7/187;
(Continued)

(56) References Cited

U.S. PATENT DOCUMENTS

| | | | |
|---|---|---|---|
| 6,842,638 B1 * | 1/2005 | Suri et al. ................. | G06T 7/64 600/431 |
| 7,889,912 B2 * | 2/2011 | Orderud ..................... | G06T 7/20 382/128 |

(Continued)

FOREIGN PATENT DOCUMENTS

| | | | | | |
|---|---|---|---|---|---|
| JP | 2006-081640 A | * | 3/2006 | | |
| JP | 2008-068086 A | * | 3/2008 | ............... | G06T 7/20 |
| WO | WO-2016/143855 A1 | * | 9/2016 | ............... | G06T 7/00 |

OTHER PUBLICATIONS

Abolmaesumi et al., "Real-Time Extraction of Carotid Artery Contours from Ultrasound Images", IEEE Symp. Comp. Med. Sys., 2000, 3 pages.
(Continued)

*Primary Examiner* — Andrew W Johns
(74) *Attorney, Agent, or Firm* — The Webb Law Firm

(57) ABSTRACT

Provided is a system, method, and computer program product for segmenting vessels in an ultrasound image. The method includes detecting edges of a vessel in the ultra-
(Continued)

sound image; detecting a vessel contour of the vessel in the ultrasound image based on the detected edges and a distance regularized level set evolution; and tracking the vessel contour with a Kalman Filter.

19 Claims, 4 Drawing Sheets

(52) U.S. Cl.
CPC ... *G16H 30/40* (2018.01); *G06T 2207/10081* (2013.01); *G06T 2207/30101* (2013.01)

(58) Field of Classification Search
CPC . G06T 7/20; G06T 7/277; G06T 2207/20116; G06T 2207/30101; G06V 10/26; G06V 10/267; G06V 2201/03; G06V 2201/031; G16H 30/40; A61B 8/08; A61B 8/0891
See application file for complete search history.

(56) References Cited

U.S. PATENT DOCUMENTS

| | | |
|---|---|---|
| 2008/0069445 A1 | 3/2008 | Weber |
| 2012/0128223 A1 | 5/2012 | Rivaz et al. |
| 2013/0096434 A1 | 4/2013 | Mehi et al. |
| 2013/0267846 A1 | 10/2013 | Patwardhan et al. |
| 2013/0343626 A1 | 12/2013 | Rico et al. |

OTHER PUBLICATIONS

Belaid et al., "Phase-Based Level Set Segmentation of Ultrasound Images", IEEE Transactions on Information Technology in Biomedicine, Jan. 2011, pp. 138-147, vol. 15, No. 1.
Chaniot et al., "Vessel Segmentation in High-Frequency 2D/3D Ultrasound Images", IEEE Int. Ultrasonics Symp., 2016, pp. 1-4.
Fitzgibbon et al., "A Buyer's Guide to Conic Fitting", British Machine Vision Conference, 1995, 10 pages.
Guerrero et al., "Real-Time Vessel Segmentation and Tracking for Ultrasound Imaging Applications", IEEE Transaction on Medical Imaging, Aug. 2007, pp. 1079-1090, vol. 26, No. 8.
Kalman, "A New Approach to Linear Filtering and Prediction Problems", Transactions of the ASME—Journal of Basic Engineering, 82 (Series D), 1960, pp. 35-45.
Li et al., "Distance Regularized Level Set Evolution and Its Application to Image Segmentation", IEEE Transactions on Image Processing, Dec. 2010, pp. 3243-3254, vol. 19, No. 12.
Mauer, Jr. et al., "A Linear Time Algorithm for Computing Exact Euclidean Distance Transforms of Binary Images in Arbitrary Dimensions", Short Papers from IEEE Transactions on Pattern Analysis and Machine Intelligence, Feb. 2003, pp. 265-270, vol. 25, No. 2.
Prakash et al., "Segmentation and quantification of intra-ventricular/cerebral hemorrhage in CT scans by modified distance regularized level set evolution technique", Int J Comput Assist Radiol Surg., 7(5), Sep. 2012, pp. 1-24.
Smistad et al., "Real-Time Automatic Artery Segmentation, Reconstruction and Registration for Ultrasound-Guided Regional Anaesthesia of the Femoral Nerve", IEEE Transactions of Medical Imaging, Mar. 2016, pp. 752-761, vol. 35, No. 3.
Stetten et al., "Descending Variance Graphs for Segmenting Neurological Structures", IEEE Proceedings of the 3rd International Workshop on Pattern Recognition in NeuroImaging, Jul. 2013, 4 pages.
Tomasi et al., "Bilateral Filtering for Gray and Color Images", Proceedings of the 1998 IEEE International Conference on Computer Vision, 1998, 8 pages.
Wang et al., "Fully Automated Common Carotid Artery and Internal Jugular Vein Identification and Tracking using B-Mode Ultrasound", IEEE Trans Biomed Eng., 56(6), Jun. 2009, pp. 1691-1699.

\* cited by examiner

SYSTEM AND METHOD FOR VESSEL SEGMENTATION

CROSS-REFERENCE TO RELATED APPLICATIONS

This application is the United States national phase of International Application No. PCT/US2020/037495 filed Jun. 12, 2020, and claims priority to U.S. Provisional Patent Application No. 62/860,381 filed Jun. 12, 2019, the disclosures of which are hereby incorporated by reference in their entirety.

GOVERNMENT LICENSE RIGHTS

This invention was made with government support under W81XWH-14-1-0370 and W81XWH-14-1-0371 awarded by U.S. ARMY MEDICAL RESEARCH ACQUISITION ACTIVITY (USAMRAA). The government has certain rights in the invention.

BACKGROUND

1. Field

This disclosure relates generally to segmentation of vessels and other similar/tubular anatomic structures and, in non-limiting embodiments, to systems and methods for segmenting vessels in ultrasound images.

2. Technical Considerations

Ultra High Frequency Ultrasound (UHFUS) enables the visualization of highly deformable small and medium vessels in the hand. Intricate vessel-based measurements, such as intimal wall thickness and vessel wall compliance, require sub-millimeter vessel tracking between B-scans. Existing methods are incapable of accurately tracking vessels with such precision or in current UHFUS images which contain increased noise and speckle. Existing methods for high frequency ultrasound (HFUS) images typically require specific image-acquisition parameters, and if the parameters are adjusted to obtain a satisfactory image, then these methods do not maintain their accuracy/performance.

SUMMARY

According to non-limiting embodiments or aspects, provided is a method for segmenting vessels in an ultrasound image, comprising: detecting edges of a vessel in the ultrasound image; detecting a vessel contour of the vessel in the ultrasound image based on the detected edges and a distance regularized level set evolution; and tracking the vessel contour with a Kalman Filter.

In non-limiting embodiments or aspects, the vessel contour is detected and tracked while the vessel is deforming. In non-limiting embodiments or aspects, the ultrasound image comprises a High Frequency Ultrasound (HFUS) image or an Ultra High Frequency Ultrasound (UHFUS) image. In non-limiting embodiments or aspects, the method further comprises: downsampling the ultrasound image; and smoothing amplitude noise in the ultrasound image. In non-limiting embodiments or aspects, the amplitude noise is smoothed using a bilateral filter. In non-limiting embodiments or aspects, the ultrasound image comprises a sequence of ultrasound images of the vessel, further comprising: receiving user input identifying a pixel location inside a lumen of the vessel in at least one ultrasound image of the sequence of ultrasound images; and storing the pixel location, the ultrasound image is segmented based on using the pixel location as a seed. In non-limiting embodiments or aspects, wherein tracking the vessel contour further comprises processing each subsequent ultrasound image in the sequence of ultrasound images using the pixel location as an initialization point.

According to non-limiting embodiments or aspects, provided is a system for segmenting vessels in an ultrasound image, comprising a computing device programmed or configured to: detect edges of a vessel in the ultrasound image; detect a vessel contour of the vessel in the ultrasound image based on the detected edges and a distance regularized level set evolution; and track the vessel contour with a Kalman Filter.

In non-limiting embodiments or aspects, the vessel contour is detected and tracked while the vessel is deforming. In non-limiting embodiments or aspects, the ultrasound image comprises a High Frequency Ultrasound (HFUS) image or an Ultra High Frequency Ultrasound (UHFUS) image. In non-limiting embodiments or aspects, the computing device is programmed or configured to: downsample the ultrasound image; and smooth amplitude noise in the ultrasound image. In non-limiting embodiments or aspects, the amplitude noise is smoothed using a bilateral filter. In non-limiting embodiments or aspects, the ultrasound image comprises a sequence of ultrasound images of the vessel, and the computing device is programmed or configured to: receive user input identifying a pixel location inside a lumen of the vessel in at least one ultrasound image of the sequence of ultrasound images; and store the pixel location, the ultrasound image is segmented based on using the pixel location as a seed. In non-limiting embodiments or aspects, wherein tracking the vessel contour further comprises processing each subsequent ultrasound image in the sequence of ultrasound images using the pixel location as an initialization point.

According to non-limiting embodiments or aspects, provided is a computer program product for segmenting ultrasound images, comprising a non-transitory computer-readable medium including program instructions that, when executed by at least one processor, cause the at least one processor to: detect edges of a vessel in the ultrasound image; detect a vessel contour of the vessel in the ultrasound image based on the detected edges and a distance regularized level set evolution; and track the vessel contour with a Kalman Filter.

According to non-limiting embodiments or aspects, provided is a method for segmenting an elongated structure in an image generated by an imaging device, comprising: detecting, with at least one computing device, edges of the elongated structure in the image; detecting, with at least one computing device, a contour of the elongated structure in the image based on the detected edges and a distance regularized level set evolution; and tracking, with at least one computing device, the contour with a Kalman Filter. In non-limiting embodiments or aspects, the contour is detected and tracked while the elongated structure is deforming.

In non-limiting embodiments or aspects, the image comprises a High Frequency Ultrasound (HFUS) image or an Ultra High Frequency Ultrasound (UHFUS) image. In non-limiting embodiments or aspects, the method further comprises: downsampling the image; and smoothing amplitude noise in the image. In non-limiting embodiments or aspects, the amplitude noise is smoothed using a bilateral filter. In non-limiting embodiments or aspects, the image comprises a sequence of ultrasound images of the elongated structure, further comprising: receiving user input identifying a pixel location inside a portion of the elongated structure in at least one ultrasound image of the sequence of ultrasound images; and storing the pixel location, the ultrasound image is segmented based on using the pixel location as a seed. In non-limiting embodiments or aspects, tracking the contour further comprises processing each subsequent ultrasound image in the sequence of ultrasound images using the pixel location as an initialization point. In non-limiting embodiments or aspects, the method further comprises clustering a plurality of pixels into a cluster to reduce noise in the image. In non-limiting embodiments or aspects, the edges of the elongated structure are detected based on local phase analysis. In non-limiting embodiments or aspects, the local phase analysis is performed using a Cauchy filter or any other type of filter.

According to non-limiting embodiments or aspects, provided is a system for segmenting an elongated structure in an image generated by an imaging device, comprising a computing device programmed or configured to: detect edges of the elongated structure in the image; detect a contour of the elongated structure in the image based on the detected edges and a distance regularized level set evolution; and track the contour with a Kalman Filter.

According to non-limiting embodiments or aspects, provided is a computer program product for segmenting an elongated structure in an image generated by an imaging device, comprising a non-transitory computer-readable medium including program instructions that, when executed by at least one processor, cause the at least one processor to: detect edges of the elongated structure in the image; detect a contour of the elongated structure in the image based on the detected edges and a distance regularized level set evolution; and track the contour with a Kalman Filter.

Further non-limiting embodiments or aspects are set forth in the following numbered clauses:

Clause 1: A method for segmenting vessels in an ultrasound image, comprising: detecting, with at least one computing device, edges of a vessel in the ultrasound image; detecting, with at least one computing device, a vessel contour of the vessel in the ultrasound image based on the detected edges and a distance regularized level set evolution; and tracking, with at least one computing device, the vessel contour with a Kalman Filter.

Clause 2: The method of clause 1, wherein the vessel contour is detected and tracked while the vessel is deforming.

Clause 3: The method of clauses 1 or 2, wherein the ultrasound image comprises a High Frequency Ultrasound (HFUS) image or an Ultra High Frequency Ultrasound (UHFUS) image.

Clause 4: The method of any of clauses 1-3, further comprising: downsampling the ultrasound image; and smoothing amplitude noise in the ultrasound image.

Clause 5: The method of any of clauses 1-4, wherein the amplitude noise is smoothed using a bilateral filter.

Clause 6: The method of any of clauses 1-5, wherein the ultrasound image comprises a sequence of ultrasound images of the vessel, further comprising: receiving user input identifying a pixel location inside a lumen of the vessel in at least one ultrasound image of the sequence of ultrasound images; and storing the pixel location, wherein the ultrasound image is segmented based on using the pixel location as a seed.

Clause 7: The method of any of clauses 1-6, wherein tracking the vessel contour further comprises processing each subsequent ultrasound image in the sequence of ultrasound images using the pixel location as an initialization point.

Clause 8: The method of any of clauses 1-7, further comprising clustering a plurality of pixels into a cluster to reduce noise in the ultrasound image.

Clause 9: The method of any of clauses 1-8, wherein the edges of the vessel are detected based on local phase analysis.

Clause 10: The method of any of clauses 1-9, wherein the local phase analysis is performed using a Cauchy filter or any other type of filter.

Clause 11: A system for segmenting vessels in an ultrasound image, comprising a computing device programmed or configured to: detect edges of a vessel in the ultrasound image; detect a vessel contour of the vessel in the ultrasound image based on the detected edges and a distance regularized level set evolution; and track the vessel contour with a Kalman Filter.

Clause 12: The system of clause 11, wherein the vessel contour is detected and tracked while the vessel is deforming.

Clause 13: The system of clauses 11 or 12, wherein the ultrasound image comprises a High Frequency Ultrasound (HFUS) image or an Ultra High Frequency Ultrasound (UHFUS) image.

Clause 14: The system of any of clauses 11-13, wherein the computing device is programmed or configured to: downsample the ultrasound image; and smooth amplitude noise in the ultrasound image.

Clause 15: The system of any of clauses 11-14, wherein the amplitude noise is smoothed using a bilateral filter.

Clause 16: The system of any of clauses 11-15, wherein the ultrasound image comprises a sequence of ultrasound images of the vessel, and wherein the computing device is programmed or configured to: receive user input identifying a pixel location inside a lumen of the vessel in at least one ultrasound image of the sequence of ultrasound images; and store the pixel location, wherein the ultrasound image is segmented based on using the pixel location as a seed.

Clause 17: The system of any of clauses 11-16, wherein tracking the vessel contour further comprises processing each subsequent ultrasound image in the sequence of ultrasound images using the pixel location as an initialization point.

Clause 18: The system of any of clauses 11-17, wherein the computing device is programmed or configured to: cluster a plurality of pixels into a cluster to reduce noise in the ultrasound image.

Clause 19: The system of any of clauses 11-18, wherein the edges of the vessel are detected based on local phase analysis.

Clause 20: The system of any of clauses 11-19, wherein the local phase analysis is performed using a Cauchy filter or any other type of filter.

Clause 21: A computer program product for segmenting ultrasound images, comprising a non-transitory computer-readable medium including program instructions that, when executed by at least one processor, cause the at least one processor to: detect edges of a vessel in the ultrasound image; detect a vessel contour of the vessel in the ultrasound image based on the detected edges and a distance regularized level set evolution; and track the vessel contour with a Kalman Filter.

Clause 22: The computer program product of clause 21, wherein the vessel contour is detected and tracked while the vessel is deforming.

Clause 23: The computer program product of clauses 21 or 22, wherein the ultrasound image comprises a High Frequency Ultrasound (HFUS) image or an Ultra High Frequency Ultrasound (UHFUS) image.

Clause 24: The computer program product of any of clauses 21-23, wherein the program instructions further cause the computing device to: downsample the ultrasound image; and smooth amplitude noise in the ultrasound image.

Clause 25: The computer program product of any of clauses 21-24, wherein the amplitude noise is smoothed using a bilateral filter.

Clause 26: The computer program product of any of clauses 21-25, wherein the ultrasound image comprises a sequence of ultrasound images of the vessel, and wherein the program instructions further cause the computing device to: receive user input identifying a pixel location inside a lumen of the vessel in at least one ultrasound image of the sequence of ultrasound images; and store the pixel location, wherein the ultrasound image is segmented based on using the pixel location as a seed.

Clause 27: The computer program product of any of clauses 21-26, wherein tracking the vessel contour further comprises processing each subsequent ultrasound image in the sequence of ultrasound images using the pixel location as an initialization point.

Clause 28: The computer program product of any of clauses 21-27, wherein the program instructions further cause the computing device to: cluster a plurality of pixels into a cluster to reduce noise in the ultrasound image.

Clause 29: The computer program product of any of clauses 21-28, wherein the edges of the vessel are detected based on local phase analysis.

Clause 30: The computer program product of any of clauses 21-29, wherein the local phase analysis is performed using a Cauchy filter or any other type of filter.

Clause 31: A method for segmenting an elongated structure in an image generated by an imaging device, comprising: detecting, with at least one computing device, edges of the elongated structure in the image; detecting, with at least one computing device, a contour of the elongated structure in the image based on the detected edges and a distance regularized level set evolution; and tracking, with at least one computing device, the contour with a Kalman Filter.

Clause 32: The method of clause 31, wherein the contour is detected and tracked while the elongated structure is deforming.

Clause 33: The method of clauses 31 or 32, wherein the image comprises a High Frequency Ultrasound (HFUS) image or an Ultra High Frequency Ultrasound (UHFUS) image.

Clause 34: The method of any of clauses 31-33, further comprising: downsampling the image; and smoothing amplitude noise in the image.

Clause 35: The method of any of clauses 31-34, wherein the amplitude noise is smoothed using a bilateral filter.

Clause 36: The method of any of clauses 31-35, wherein the image comprises a sequence of ultrasound images of the elongated structure, further comprising: receiving user input identifying a pixel location inside a portion of the elongated structure in at least one ultrasound image of the sequence of ultrasound images; and storing the pixel location, wherein the ultrasound image is segmented based on using the pixel location as a seed.

Clause 37: The method of any of clauses 31-36, wherein tracking the contour further comprises processing each subsequent ultrasound image in the sequence of ultrasound images using the pixel location as an initialization point.

Clause 38: The method of any of clauses 31-37, further comprising clustering a plurality of pixels into a cluster to reduce noise in the image.

Clause 39: The method of any of clauses 31-38, wherein the edges of the elongated structure are detected based on local phase analysis.

Clause 40: The method of any of clauses 31-39, wherein the local phase analysis is performed using a Cauchy filter or any other type of filter.

Clause 41: A system for segmenting an elongated structure in an image generated by an imaging device, comprising a computing device programmed or configured to: detect edges of the elongated structure in the image; detect a contour of the elongated structure in the image based on the detected edges and a distance regularized level set evolution; and track the contour with a Kalman Filter.

Clause 42: A computer program product for segmenting an elongated structure in an image generated by an imaging device, comprising a non-transitory computer-readable medium including program instructions that, when executed by at least one processor, cause the at least one processor to: detect edges of the elongated structure in the image; detect a contour of the elongated structure in the image based on the detected edges and a distance regularized level set evolution; and track the contour with a Kalman Filter.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

Additional advantages and details are explained in greater detail below with reference to the non-limiting, exemplary embodiments that are illustrated in the accompanying figures, in which.

DETAILED DESCRIPTION

Figure 1:
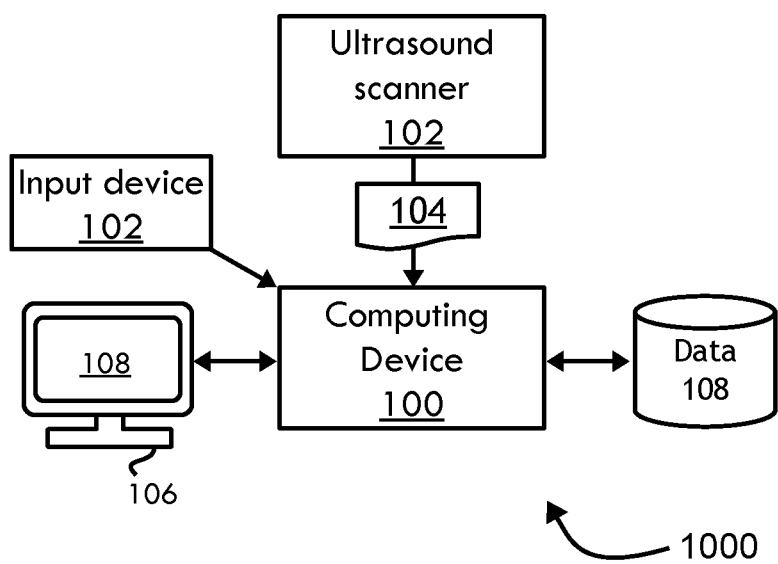
FIG. 1 illustrates a system for segmenting vessels in an ultrasound image according to non-limiting embodiments.

It is to be understood that the embodiments may assume various alternative variations and step sequences, except where expressly specified to the contrary. It is also to be understood that the specific devices and processes described in the following specification, are simply exemplary embodiments or aspects of the disclosure. Hence, specific dimensions and other physical characteristics related to the embodiments or aspects disclosed herein are not to be considered as limiting. No aspect, component, element, structure, act, step, function, instruction, and/or the like used herein should be construed as critical or essential unless explicitly described as such. Also, as used herein, the articles "a" and "an" are intended to include one or more items and may be used interchangeably with "one or more" and "at least one." Also, as used herein, the terms "has," "have," "having," or the like are intended to be open-ended terms. Also, as used herein, the term "patient" may refer to a human, animal, or other specimen being imaged. Also, as used herein, the term "ultrasound" may refer to traditional ultrasound machine, or other related imaging device such as opto-acoustic imaging, acousto-optical imaging, optical-coherence tomography, etc. Also, as used herein, "vessel" may refer to any anatomic structure of similar shape and features, such as ligaments, nerve bundles, etc. Also, as used herein, the term "Kalman Filter" includes regular "Kalman Filters" and "Extended Kalman Filters" (EKF). Further, the phrase "based on" is intended to mean "based at least partially on" unless explicitly stated otherwise.

As used herein, the term "computing device" may refer to one or more electronic devices configured to process data. A computing device may, in some examples, include the necessary components to receive, process, and output data, such as a processor, a display, a memory, an input device, a network interface, and/or the like. A computing device may be a mobile device. A computing device may also be a desktop computer or other form of non-mobile computer. In non-limiting embodiments, a computing device may include a GPU. In non-limiting embodiments, a computing device may be comprised of a plurality of circuits.

Non-limiting embodiments provide for a system and method for segmenting anatomical structures in an image generated by an imaging device. Although some of the non-limiting examples discussed herein relate to segmenting vessels in ultrasound images (including HFUS and/or UHFUS), it will be appreciated that the systems and methods discussed herein may be used for segmenting a variety of different anatomical structures, including but not limited to elongated structures (ligaments, nerves, and/or the like), from a variety of different types of images (opto-acoustic images, acousto-optical images, Optical-Coherence Tomography (OCT) images, and/or the like). Thus, where a "vessel" and "ultrasound image" are referenced in the examples below, those skilled in the art will understand that other anatomical structures and images may be used.

Non-limiting embodiments allow for tracking such anatomical structures in an image in a manner that works rapidly and allows for real-time tracking of a vessel contour in a sequence of ultrasound images. As an example, non-limiting embodiments provide for faster speeds, for example >50 frames per second, for tracking vessels in ultrasound images. Moreover, non-limiting embodiments provide for a system and method for segmenting vessels and other anatomical structures in an ultrasound image or other image using a combination of local phase analysis for edge detection, a distance-regularized level set for vessel contour detection, and an Kalman Filter (including an Extended Kalman Filter (EKF)) to track the vessel contour. Accordingly, a deforming vessel may be segmented and tracked quickly and with precision, efficiently using computing resources and providing real-time visibility.

In non-limiting embodiments, the system and method for segmenting vessels may also be performed with Ultra High Frequency Ultrasound (UHFUS) images, although it will be appreciated that any ultrasound image may be used. Technical problems arising with UHFUS, such as increased speckle noise, may be improved using non-limiting embodiments of the system and method for segmenting vessels described herein. Moreover, in non-limiting embodiments, a sequence of ultrasound images are processed to track the contours of the deformation of the vessel over time.

Referring now to FIG. 1, shown is a system 1000 for segmenting vessels in an ultrasound image according to non-limiting embodiments. The system 1000 includes an ultrasound scanner 102 that outputs one or more ultrasound images 104. The ultrasound scanner may be, for example, a UHFUS scanner, although a regular, HFUS, or other type of ultrasound scanner may also be used. The ultrasound scanner 102 is in communication with a computing device 100 and, during operation, the ultrasound scanner 102 communicates a sequence of ultrasound images to the computing device 100 while the ultrasound scanner 102 is operated. In some examples, the vessels being imaged with the ultrasound scanner 102 may deform (e.g., move, twist, bend, reshape, and/or the like). The ultrasound scanner 102 may be in communication with one or more ultrasound probes (not shown in FIG. 1) for scanning a patient. The computing device 100 is in communication with a data storage device 109 that may store received images and/or processed images.

With continued reference to FIG. 1, a display device 106 displays one or more ultrasound images 104 on a user interface 108 based on data received from the computing device 100. A user manipulates an input device 101, such as a mouse, keyboard, trackball, touchscreen, and/or the like, to interact with the user interface 108. In some examples, the display device 106 may be a computing device independent from computing device 100, in which case the input device 101 may be in communication with the display device 106. A user may be an operator of the ultrasound scanner 102 and may utilize the input device 101 and user interface 108 to select one or more pixels on an ultrasound image, displayed on the display device 106, that are part of a vessel to be segmented and tracked. Based on this input, the computing device 100 detects the edges of the vessel, the contour(s) of the vessel, and tracks the vessel.

Figure 2:
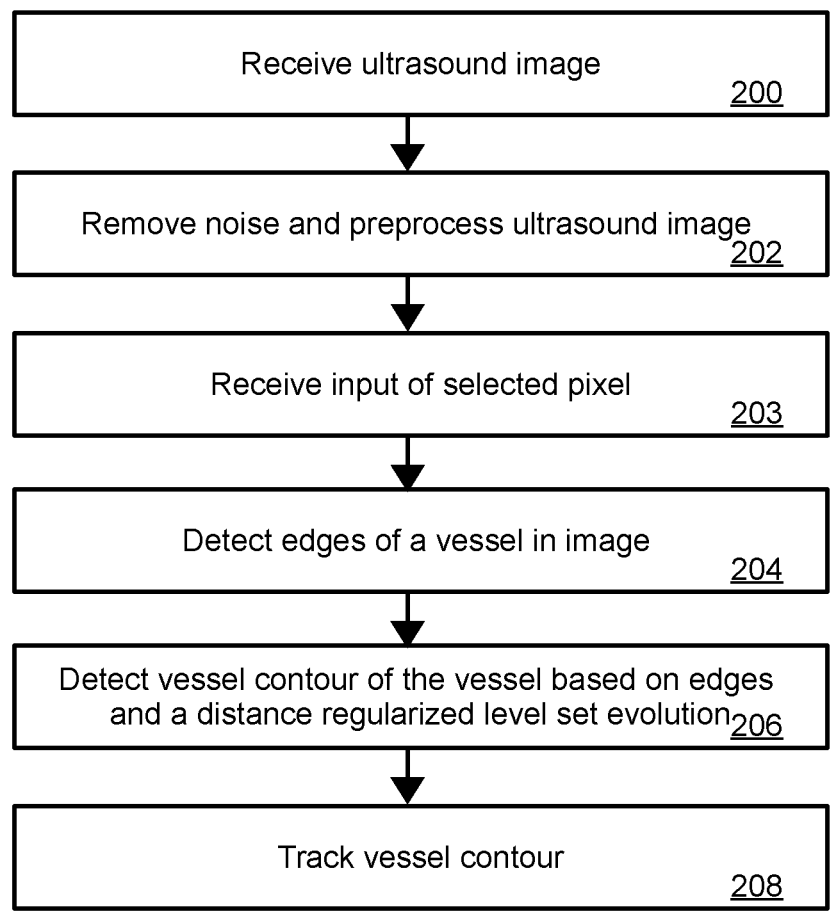
FIG. 2 illustrates a flow diagram of a method for segmenting vessels in an ultrasound image according to non-limiting embodiments.
Figure 3:
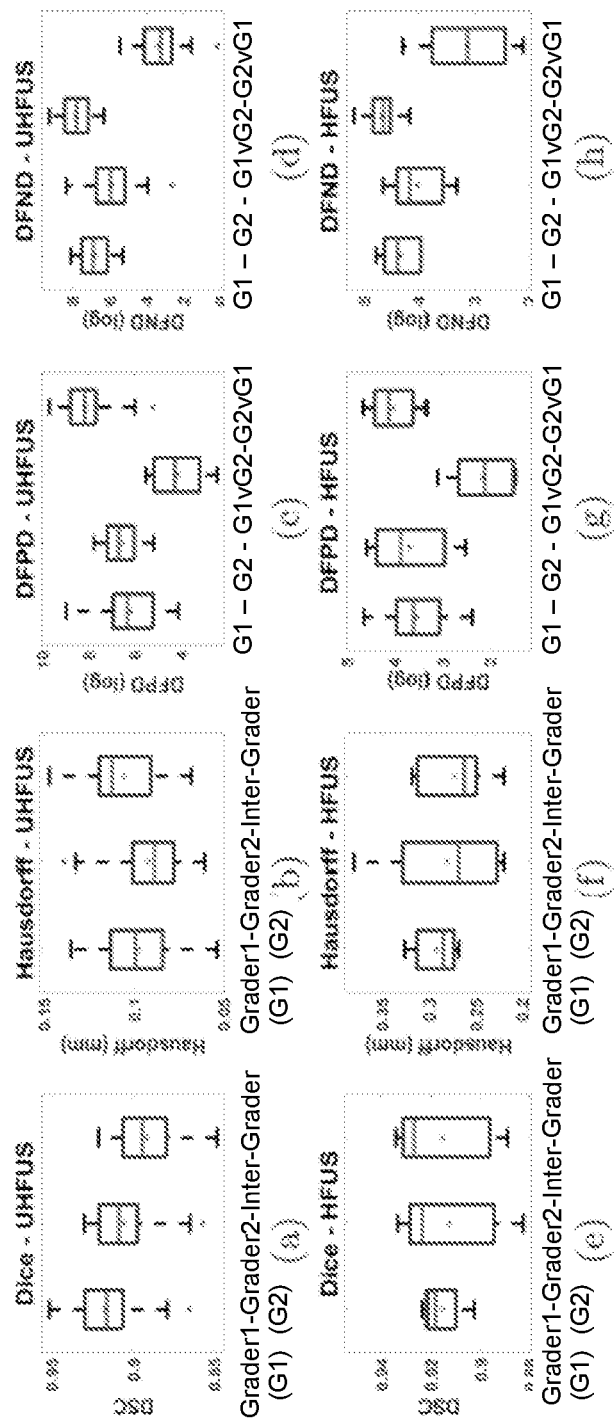
FIGS. 3(a)-(h) show test data of the results of an implementation according to non-limiting embodiments.

Still referring to FIG. 1, the display device 106 may display the tracked and segmented vessel to the operator. Such display may be in real-time (e.g., while a probe is actively scanning a patient) or may be performed after the sequence of ultrasound images is captured. The display may show a segmented and tracked vessel. For example, the display device 106 may display an ultrasound image with one or more annotations or modifications, such as lines, highlights, colored regions, shapes, and/or the like, the visually differentiate between vessels. As an example, a selected vessel may be highlighted and remain highlighted throughout various deformations by being tracked. A user may select one or more options Referring now to FIG. 2, shown is a method for segmenting vessels in an ultrasound image according to non-limiting embodiments. It will be appreciated that the steps shown in FIG. 2 are for illustration purposes only and that non-limiting embodiments may involve more steps, fewer steps, different steps, and/or a different order of steps. At a first step 200, one or more ultrasound images are received by a computing device as input. As explained herein, an HFUS or UHFUS scanner may be used to capture one or more ultrasound images. The ultrasound images may represent vessels, having boundaries and shapes, as an operator of the ultrasound moves a probe over a patient's body. The ultrasound images may also be from a fixed probe. A sequence of numerous ultrasound images may represent a wide range of motions with the probe, such as longitudinal scanning, out-of-plane tissue deformation, beating vessel visualization, and/or the like. A sequence may be a number of scans with a specified dimension, such as 100 2D B-scans with dimensions of 832×512 pixels. Various other sequence types are possible.

At step 202, the input ultrasound image(s) are processed to reduce noise. Implementations using UHFUS images may introduce greater amounts of speckle noise than HFUS, for example. To mitigate the effects of speckle noise during segmentation and to speed up computation, the images may be first downsampled (e.g., by a factor of 4 or other suitable factor) in each dimension. Next, a bilateral filter (e.g., of size 5×5 pixels or other suitable size) may be applied to the downsampled image to smooth the small amplitude noise while preserving vessel boundaries that are used for segmentation. Step 202 may result in a bilateral filtered image.

In some non-limiting embodiments, the ultrasound image may be processed to cluster pixels. For example, the pixels may be clustered into homogeneous patches. Each pixel may be represented by two elements: the mean intensity of the patch that it belongs to, and a cluster/patch center (e.g., root). For each pixel in the starting image (e.g., the bilateral filtered image if the image is first filtered), the mean intensity and variance is found in a circular neighborhood. The appropriate diameter of the circular neighborhood varies depending on the size of the vessel to be tracked. For small vessels in UHFUS images (e.g., ≤70 pixel diameter or 0.81 mm), the neighborhood size may be 3×3 pixels, for example, and 7×7 pixels for larger vessels (e.g., >70 pixel diameter). Each patch root in the resulting clustered image has the lowest local variance amongst all the members of the same patch. Roots in the clustered image may be used as seeds to track vessels over sequential images. Increasing the neighborhood size reduces the number of roots that can be tracked, which can cause tracking failure when large motion occurs.

At step 203, input from a user is received that identifies a pixel on the image for initialization. The selected pixel may identify a vessel lumen in an image that precedes a sequence of other images. For example, a user may input a point by selecting (clicking, touching, and/or the like) on the image with an input device such that the point corresponds to a pixel within the vessel lumen. This pixel location may be stored as a seed, denoted by $s^0$ at time t=0, to segment the vessel boundary in the first image (or any image that precedes a sequence of other images), and to initialize the vessel lumen tracking in subsequent images. In some examples, step 203 may be performed after the edges of one or more vessels are detected in step 204.

At step 204 of FIG. 2, the ultrasound image is processed to detect the edges of the vessel. In non-limiting embodiments, the ultrasound image (e.g., the bilateral filtered image output by step 202) may be first processed to highlight vessel boundaries. For example, a Cauchy filter may be used to process the image to detect the edges. The spatial intensity value at a location $x=[x\ y]^T$ in the image 1B is denoted by $I_B(x)$. After applying a 2D Fourier transform, the corresponding 2D frequency domain value is F(w), where $w=[w1\ w2]^T$. The Cauchy filter C(w) applied to F(w) is represented as C(w) in Eq. (1):

$$C(w)=\|w\|_2^u \exp(-w_o\|w\|_2), u \geq 1 \tag{1}$$

In Eq. (1), u is a scaling parameter and $w_o$ is the center frequency. Filtering F(w) with C(w) yields the monogenic signal, from which the feature asymmetry map ($I_{FA}$) may be obtained. Pixel values in $I_{FA}$ range between [0, 1].

At step 206 of FIG. 2, once the edges of the vessel are detected, the vessel contour may be detected to segment the vessel based on the edges and a distance regularized level set evolution. To detect the vessel contour, an initial boundary segmentation may be performed. For example, a number of radial lines (e.g., 360 radial lines of maximum search length M=100 pixels) may stem from so to the vessel boundaries in $I_{FA}$. The first local maximum on each radial line may be included in a set I as an initial boundary point. Once an initial boundary segmentation is performed, an estimate of the semi-major and semi-minor vessel axes may be determined by fitting an ellipse to the initial boundary locations in I. Next, the estimated values may be shrunk (e.g., by 75% as an example, which would place more of the shrunk estimate on the inside rather than outside of the vessel boundary) and used to initialize an elliptical binary level set function (LSF) $\varphi_o$ in a narrowband distance regularized level set evolution (DRLSE) framework. As the LSF initialization is close to the true boundaries, the DRLSE formulation allows quick propagation of LSF to the desired vessel locations with a large timestep ΔT. The DRLSE framework minimizes an energy functional E(φ) using the gradient defined in Eq. (2) below:

$$\frac{\partial \phi}{\partial \tau} = \mu div(d_p(|\nabla \phi|)\nabla \phi) + \lambda \delta_\epsilon(\phi) div\left(g \frac{\nabla \phi}{|\nabla \phi|}\right) + \alpha g \delta_\epsilon(\phi) \tag{2}$$

In Eq. (2), μ, λ, E, and α are constants, g is an edge indicator function, and $\delta_E$ and $d_p$ are first order derivatives of the Heaviside function and the double-well potential respectively. The parameters used in example datasets are: ΔT=10, μ=0.2, λ=1, α=−1, and E=1 for a total of 15 iterations, although other implementations are possible.

At step 208 of FIG. 2, the vessel contour is tracked. The vessel contour may be tracked by annotating or modifying the ultrasound image on a display device (e.g., lines, highlights, colored regions, shapes, and/or the like) as the vessel deforms. The tracking may be performed as the vessel deforms in real-time or may be performed on a recording of one or more ultrasound image sequences. To update the vessel lumen position $s^t$ at time t to $s^{t+1}$ at time t+1, two new potential seeds are found, from which one is chosen. The first seed is found using an Extended Kalman Filter. The second seed is found using $I_C$, and it is needed in case the Extended Kalman Filter fails to track the vessel lumen due to abrupt motion As a non-limiting example, the Extended Kalman Filter may track a state vector defined by: $x^t=[c^t_x, c^t_y, a^t, b^t]$, where $s_{ekt}^t=[c^t_x, c^t_y]$ is the tracked vessel lumen location and $[a^t, b^t]$ are the tracked semi-major and semi-minor vessel axes respectively. Instead of tracking all locations, it is computationally more efficient to track $x^t$, the elements of which are estimated by again fitting an ellipse to the locations in D. The Extended Kalman Filter may project the current state $x^t$ at time t to the next state $x^{t+1}$ at time t+1 using a motion model having two state transition matrices A1, A2, the covariance error matrix P, and the process-noise covariance matrix Q. These matrices may be initialized using the values in Eqs. (3)-(6) shown below:

$$A_1=\text{diag}([1.5,1.5,1.5,1.5]) \tag{3}$$

$$A_2=\text{diag}([-0.5,-0.5,-0.5,-0.5]) \tag{4}$$

$$P=\text{diag}([1000,1000,1000,1000]) \tag{5}$$

$$Q=\text{diag}([0.001,0.001,0.001,0.001]) \tag{6}$$

The second seed may be found using the clustering result. At $s^t$ in the clustered image $I_c^{t+1}$ at time t+1, the axes [$a^{t+1}$, $b^{t+1}$] tracked with the Extended Kalman Filter are used to find the neighboring roots of $s^t$ in an elliptical region of size [$1.5a^{t+1}$, $b^{t+1}$] pixels. Amongst these roots, the root $s_c^{t+1}$, which has the lowest mean pixel intensity representing a patch in the vessel lumen, is selected. By using the elliptical neighborhood derived from the Extended Kalman Filter state, $s_c^t$ is tracked in subsequent frames. The elliptical region is robust to vessel compression, which may shrink a vessel vertically and/or enlarge a vessel horizontally.

The Extended Kalman Filter prediction may be sufficient for tracking during slow longitudinal scanning or still imaging as $s_{ekf}^{t+1}$ and $s_c^{t+1}$ lie close to each other. However, when large motion is encountered, the Extended Kalman Filter prediction of the vessel location may be incorrect, leading to tracking failure. In some non-limiting embodiments, this potential error is mitigated during large vessel motion by ignoring $s_{ekf}^{t+1}$ and updating $s_c^{t+1}$ as the new tracking seed according to Eq. (7) shown below:

$$s^{t+1} = \begin{cases} s_c^{t+1} & \text{if } \|s_{ekf}^{t+1} - s_c^{t+1}\|_2 > a^{t+1} \\ s_{ekf}^{t+1} & \text{otherwise} \end{cases} \quad (7)$$

Non-limiting embodiments were evaluated for segmentation accuracy by comparing the contour segmentations against annotations of two graders. Test data for these non-limiting implementations are shown in FIGS. 3(a)-(h). The * in each box plot shown in FIGS. 3(a)-(h) represents the mean value of the metric. The terms G1vG2 and G2vG1 represent the inter-grader annotation variability when grader 2 annotation was considered the ground truth and vice versa.

One non-limiting implementation using 35 UHFUS sequences, each including 100 images, was tested. The test results for the UHFUS sequences are shown in FIGS. 3(a)-(d). As shown, the two graders varied in their estimation of the vessel boundary locations in UHFUS images due to the speckle noise obscuring the precise location of the vessel edges, as shown in the inter-grader Dice score in FIG. 3(a), inter-grader Hausdorff distance in FIG. 3(b), and inter-grader variation between FIGS. 3(c) and 3(d). Grader 2 tended to under-segment the vessel (G1vG2, low DFPD and high DFND scores), while grader 1 tended to over-segment (G2vG1, high DFPD and low DFND scores). As desired, the segmentation performed according to a non-limiting implementation tended to be within the region of uncertainty between the two graders (see FIGS. 3(c) and 3(d)). Accordingly, the mean Dice score and mean Hausdorff distance of the implementation against grader 1 (0.917±0.019, 0.097±0.019 mm) and grader 2 (0.905±0.018, 0.091±0.019 mm) were better than the inter-grader scores of (0.892±0.019, 0.105±0.02 mm). The largest observed Hausdorff distance error of 0.135 mm is 6 times smaller than the smallest observed vessel diameter of 0.81 mm. Similarly, the mean Hausdorff distance error of 0.094±0.019 mm is ~7 times smaller than smallest observed vessel diameter. This satisfies the goal of sub-mm vessel contour localization.

Test data for processing 5 HFUS sequences, each including 250 images, is shown in FIGS. 3(e)-(h). The non-limiting implementations tested demonstrated the desirable property of final segmentations that lay in the uncertain region of annotation between the two graders. This is supported by comparing the mean Dice score and mean Hausdorff distance of the implementation against grader 1 (0.915±0.008, 0.292±0.023 mm) and grader 2 (0.912±0.021, 0.281±0.065 mm), with the inter-grader scores (0.915 0.02, 0.273 0.04 mm). Moreover, a Mean Absolute Deviation (MAD) error was calculated and was shown to be ~2 times lower than the error associated with existing segmentation methods, even with the lower resolution of HFUS.

Figure 4:
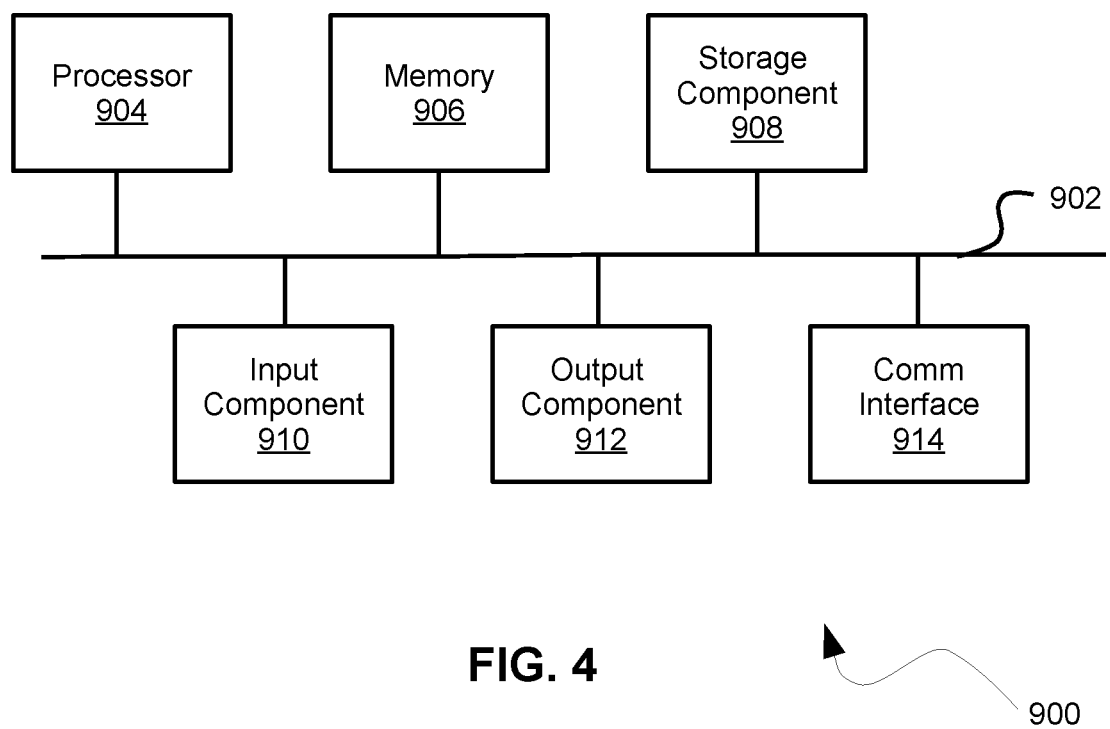
FIG. 4 illustrates example components of a computing device used in connection with non-limiting embodiments.

Referring now to FIG. 4, shown is a diagram of example components of a computing device 900 for implementing and performing the systems and methods described herein according to non-limiting embodiments. In some non-limiting embodiments, device 900 may include additional components, fewer components, different components, or differently arranged components than those shown in FIG. 4. Device 900 may include a bus 902, a processor 904, memory 906, a storage component 908, an input component 910, an output component 912, and a communication interface 914. Bus 902 may include a component that permits communication among the components of device 900. In some non-limiting embodiments, processor 904 may be implemented in hardware, firmware, or a combination of hardware and software. For example, processor 904 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 906 may include random access memory (RAM), read only memory (ROM), and/or another type of dynamic or static storage device (e.g., flash memory, magnetic memory, optical memory, etc.) that stores information and/or instructions for use by processor 904.

With continued reference to FIG. 4, storage component 908 may store information and/or software related to the operation and use of device 900. For example, storage component 908 may include a hard disk (e.g., a magnetic disk, an optical disk, a magneto-optic disk, a solid state disk, etc.) and/or another type of computer-readable medium. Input component 910 may include a component that permits device 900 to receive information, such as via user input (e.g., a touch screen display, a keyboard, a keypad, a mouse, a button, a switch, a microphone, etc.). Additionally, or alternatively, input component 910 may include a sensor for sensing information (e.g., a global positioning system (GPS) component, an accelerometer, a gyroscope, an actuator, etc.). Output component 912 may include a component that provides output information from device 900 (e.g., a display, a speaker, one or more light-emitting diodes (LEDs), etc.). Communication interface 914 may include a transceiver-like component (e.g., a transceiver, a separate receiver and transmitter, etc.) that enables device 900 to communicate with other devices, such as via a wired connection, a wireless connection, or a combination of wired and wireless connections. Communication interface 914 may permit device 900 to receive information from another device and/or provide information to another device. For example, communication interface 914 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 900 may perform one or more processes described herein. Device 900 may perform these processes based on processor 904 executing software instructions stored by a computer-readable medium, such as memory 906 and/or storage component 908. A computer-readable medium may include any non-transitory memory device. A memory device includes memory space located inside of a single physical storage device or memory space spread across multiple physical storage devices. Software instructions may be read into memory 906 and/or storage component 908 from another computer-readable medium or from another device via communication interface 914. When executed, software instructions stored in memory 906 and/or storage component 908 may cause processor 904 to perform one or more processes described herein. Additionally, or alternatively, hardwired circuitry may be used in place of or in combination with software instructions to perform one or more processes described herein. Thus, embodiments described herein are not limited to any specific combination of hardware circuitry and software. The term "programmed or configured," as used herein, refers to an arrangement of software, hardware circuitry, or any combination thereof on one or more devices.

Although embodiments have been described in detail for the purpose of illustration, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A method for segmenting vessels in an ultrasound image, comprising:
    detecting, with at least one computing device, edges of a vessel in the ultrasound image, wherein the edges of the vessel are detected based on local phase analysis;
    detecting, with at least one computing device, a vessel contour of the vessel in the ultrasound image based on the detected edges and a distance regularized level set evolution; and
    tracking, with at least one computing device, the vessel contour with a Kalman Filter.

2. The method of claim 1, wherein the vessel contour is detected and tracked while the vessel is deforming.

3. The method of claim 1, wherein the ultrasound image comprises a High Frequency Ultrasound (HFUS) image or an Ultra High Frequency Ultrasound (UHFUS) image.

4. The method of claim 1, further comprising:
    downsampling the ultrasound image; and
    smoothing amplitude noise in the ultrasound image.

5. The method of claim 4, wherein the amplitude noise is smoothed using a bilateral filter.

6. The method of claim 1, wherein the ultrasound image comprises a sequence of ultrasound images of the vessel, further comprising:
    receiving user input identifying a pixel location inside a lumen of the vessel in at least one ultrasound image of the sequence of ultrasound images; and
    storing the pixel location, wherein the ultrasound image is segmented based on using the pixel location as a seed.

7. The method of claim 6, wherein tracking the vessel contour further comprises processing each subsequent ultrasound image in the sequence of ultrasound images using the pixel location as an initialization point.

8. The method of claim 1, further comprising clustering a plurality of pixels into a cluster to reduce noise in the ultrasound image.

9. The method of claim 1, wherein the local phase analysis is performed using a Cauchy filter or any other type of filter.

10. A system for segmenting vessels in an ultrasound image, comprising a computing device programmed or configured to:
    detect edges of a vessel in the ultrasound image, wherein the edges of the vessel are detected based on local phase analysis;
    detect a vessel contour of the vessel in the ultrasound image based on the detected edges and a distance regularized level set evolution; and
    track the vessel contour with a Kalman Filter.

11. The system of claim 10, wherein the vessel contour is detected and tracked while the vessel is deforming.

12. The system of claim 10, wherein the ultrasound image comprises a High Frequency Ultrasound (HFUS) image or an Ultra High Frequency Ultrasound (UHFUS) image.

13. The system of claim 10, wherein the computing device is programmed or configured to:
    downsample the ultrasound image; and
    smooth amplitude noise in the ultrasound image.

14. The system of claim 13, wherein the amplitude noise is smoothed using a bilateral filter.

15. The system of claim 10, wherein the ultrasound image comprises a sequence of ultrasound images of the vessel, and wherein the computing device is programmed or configured to:
    receive user input identifying a pixel location inside a lumen of the vessel in at least one ultrasound image of the sequence of ultrasound images; and
    store the pixel location, wherein the ultrasound image is segmented based on using the pixel location as a seed.

16. The system of claim 15, wherein tracking the vessel contour further comprises processing each subsequent ultrasound image in the sequence of ultrasound images using the pixel location as an initialization point.

17. The system of claim 10, wherein the computing device is programmed or configured to: cluster a plurality of pixels into a cluster to reduce noise in the ultrasound image.

18. The system of claim 10, wherein the local phase analysis is performed using a Cauchy filter or any other type of filter.

19. A computer program product for segmenting a sequence of ultrasound images of a vessel, comprising a non-transitory computer-readable medium including program instructions that, when executed by at least one processor, cause the at least one processor to:
    receive user input identifying a pixel location inside a lumen of the vessel in an ultrasound image of a sequence of ultrasound images;
    store the pixel location;
    detect edges of the vessel in the ultrasound image;
    detect a vessel contour of the vessel in the ultrasound image based on the detected edges and a distance regularized level set evolution; and
    track the vessel contour with a Kalman Filter, wherein the ultrasound image is segmented based on using the pixel location as a seed.

* * * * *